(12) United States Patent
Cho et al.

(10) Patent No.: US 7,223,874 B2
(45) Date of Patent: May 29, 2007

(54) BICYCLIC TETRAHYDROFURAN LACTONE DERIVATIVES AND PROCESS FOR THE PREPARATION THEREOF

(75) Inventors: Yong Seo Cho, Seoul (KR); Joo Hwan Cha, Seoul (KR); Ae Nim Pae, Seoul (KR); Hun Yeong Koh, Seoul (KR); Chul Shin, Incheon (KR)

(73) Assignee: Korea Institute of Science and Technology, Seoul (KR)

( * ) Notice: Subject to any disclaimer, the term of this patent is extended or adjusted under 35 U.S.C. 154(b) by 18 days.

(21) Appl. No.: 11/303,125

(22) Filed: Dec. 15, 2005

(65) Prior Publication Data

US 2007/0010679 A1    Jan. 11, 2007

(30) Foreign Application Priority Data

Jul. 8, 2005    (KR) ...................... 10-2005-0061706

(51) Int. Cl.
*C07D 493/00*    (2006.01)
*C07D 311/02*    (2006.01)

(52) U.S. Cl. ...................... 549/283; 305/306
(58) Field of Classification Search .............. 549/306, 549/305, 283
See application file for complete search history.

(56) References Cited

OTHER PUBLICATIONS

Masayuki, Sataki, Azaspiracid, a New Marine Toxin Having Unique Spiro Ring Assemblies, Isolated from Irish Mussels, *Mytilus edulis*, J. Am. Chem. Soc., 1998,120,9967-9968.
Josep Aiguade, Synthesis of a 2,9-Dioxabicyclo[3.3.1]nonane via Double Intramolecular Hetero_Machael Addition: Entry to the F-G Ring System of the Azaspiracids, Org. Lett., 2001, 3, 979-982.
K.C. Nicolaou, Synthesis of the FGHI Ring System of Azaspiracid, Angew. Chem., Int. Ed. 2001,40, 1262-1265.
Peter Somfai, An Enantioselective Total Synthesis of (+)-Altholactone from Diethyl L-Tartrate, Tetrahedron, 1994, 50, 11315-11320.
Patricia Y. Hayes, Total Synthesis and Absolute Stereochemistry of Plakortone D, J. Am. Chem. Soc. 2002, 124,9718-9719.

*Primary Examiner*—Thomas McKenzie
*Assistant Examiner*—Raymond Covington
(74) *Attorney, Agent, or Firm*—Frommer Lawrence & Haug LLP;; Ronald R. Santucci

(57) ABSTRACT

The present invention relates to bicyclic tetrahydrofuran lactone derivatives of Formula (1) and a preparation method thereof, and particularly it relates to a process of preparing compounds of Formula (1) by performing an intramolecular cyclization of tetrahydrofuran-allenic acid derivatives in the presence of a phenyl halide, a palladium catalyst and a base:

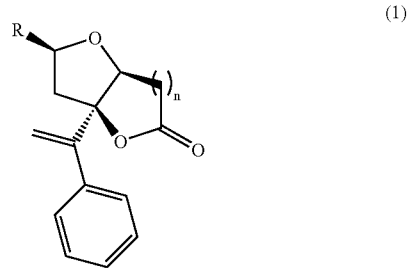

(1)

wherein n is 1 or 2, and R is phenyl optionally substituted with $C_1$–$C_6$ alkyl, $C_1$–$C_6$ alkoxy, hydroxyl or $C_1$–$C_6$ hydroxyalkyl group.

10 Claims, No Drawings

BICYCLIC TETRAHYDROFURAN LACTONE DERIVATIVES AND PROCESS FOR THE PREPARATION THEREOF

This application claims priority benefits from South Korean Patent Application No. 10-2005-0061706 filed Jul. 8, 2005.

TECHNICAL FIELD

The present invention relates to bicyclic tetrahydrofuran lactone derivatives of Formula (1) and a preparation method thereof, and particularly it relates to a process of preparing compounds of Formula (1) by performing an intramolecular cyclization of tetrahydrofuran-allenic acid derivatives in the presence of a phenyl halide, a palladium catalyst and a base:

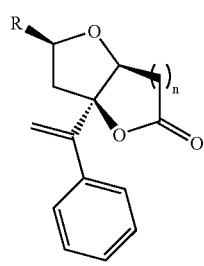

(1)

wherein n is 1 or 2, and R is phenyl optionally substituted with $C_1$–$C_6$ alkyl, $C_1$–$C_6$ alkoxy, hydroxyl or $C_1$–$C_6$ hydroxyalkyl group.

RELATED PRIOR ART

Tetrahydrofuran derivatives are known to exist in various natural substances, and are investigated as active ingredients in natural substances or synthetic drugs. Especially, stereoselective tetrahydrofuran derivatives having cis geometry at C-2,5 positions are known to have superior bioactivity. For example, bicyclic tetrahydrofuran or bicyclic perhydrofuropyran compounds serve a structural basis of various natural substances (*J. Am. Chem. Soc.*, 1998, 120, 9967–9968; *Org. Lett.*, 2001, 3, 979–982; *Angew. Chem., Int. Ed.* 2001, 40, 1262–1265).

(+)-Altholactone, extracted from *Polyalthia* or *Goniothalamus-giganteus*, is known to have cytotoxicity (in vivo) and an activity against P-338 leukemia (in vivo). (+)-Altholactone has tetrahydrofuran and lactone in its structure (*Tetrahedron*, 1994, 50, 11315–11320).

Further, plakortones A–D constitutes a new kind of SR—$Ca^{2+}$-pumping ATPase activator associated with heart disease, and participates in correction of irregularity of heart disease atony. Among these derivatives, plakortone D is known to have superior activity. Meanwhile, it was reported that plakortones B—F show in vivo cytotoxicity against fibrosarcoma infected from mice. The aforementioned plakortones also have tetrahydrofuran and lactone in their structure (*J. Am. Chem. Soc.* 2002, 124, 9718–9719).

As set forth above, the compounds with tetrahydrofuran and lactone structure are highly useful value as key materials in the pharmaceutical or fine chemical industry. Therefore, there is still a demand to develop bicyclic tetrahydrofuran lactone derivatives highly useful as key materials in the pharmaceutical or fine chemical industry, and a more efficient process for preparing the compounds.

SUMMARY OF INVENTION

In one aspect of the present invention, there are provided bicyclic tetrahydrofuran lactone derivatives with a novel-structure.

In another aspect of the present invention, there is provided a process for preparing the bicyclic tetrahydrofuran lactone derivatives by performing intramolecular cyclization of tetrahydrofuran-allenic acid derivatives in the presence of a phenyl halide, a palladium catalyst and a base.

DETAILED DESCRIPTION

In one aspect, the present invention relates to bicyclic tetrahydrofuran lactone derivatives of Formula (1):

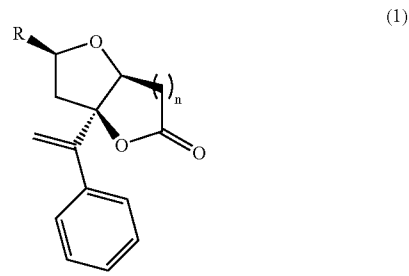

(1)

wherein n is 1 or 2, and R is phenyl optionally substituted with $C_1$–$C_6$ alkyl, $C_1$–$C_6$ alkoxy, hydroxyl or $C_1$–$C_6$ hydroxyalkyl group.

The bicyclic tetrahydrofuran lactone derivatives of the present invention are novel compounds with a novel structure and are highly useful value as active materials in the pharmaceutical or fine chemical industry.

The bicyclic tetrahydrofuran lactone derivatives of Formula (1) includes without limitation those (i) wherein n is 1, and R is phenyl optionally substituted with $C_1$–$C_6$ alkyl or $C_1$–$C_6$ alkoxy group, or (ii) wherein n is 2, and R is phenyl optionally substituted with $C_1$–$C_6$ alkyl or $C_1$–$C_6$ alkoxy group.

In another aspect, the present invention relates to a process of preparing bicyclic tetrahydrofuran lactone derivatives of Formula (1), the process comprising an intramolecular cyclization of tetrahydrofuran-allenic acid derivatives of Formula (2) in the presence of a phenyl halide, a palladium catalyst and a base:

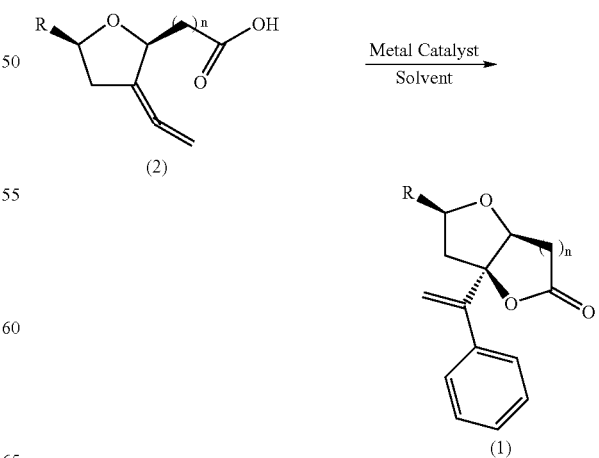

wherein n and R are as defined above.

Phenyl iodide (PhI) is preferred to be used as the phenyl halide in an amount of 1–6 equivalents with respect to the starting material, tetrahydrofuran-allenic acid derivatives of Formula (2).

Representative examples of the palladium catalyst include, but are not limited to, tetrakis(triphenylphosphin) palladium (Pd(PPh$_3$)$_4$) and palladium dichloride (PdCl$_2$). The amount of the palladium catalyst is preferred to be 0.01–1 equivalent with respect to the tetrahydrofuran-allenic acid of Formula (2).

The base is metal salt selected from carbonate, bicarbonate, sulfate and a mixture thereof, where the metal is alkali metal or alkaline earth metal. Representative examples of the base includes without limitation potassium carbonate (K$_2$CO$_3$). The base is preferred to be used in an amount of halide in an amount of 1–6 equivalents with respect to tetrahydrofuran-allenic acid derivatives of Formula (2).

Conventional organic solvents may be used in the process herein, and the representative examples of the solvents includes without limitation diethylether, tetrahydrofuran, dichloromethane, dimethylformamide, ethyl acetate, chloroform or a mixture thereof. The preferable example of the solvent is dimethylformamide.

The intramolecular cyclization is preferred to be performed at 0–90° C. for about 3–5 hours.

EXAMPLES

The present invention is described more specifically by the following Examples. Examples herein are meant only to illustrate the present invention, but in no way to limit the claimed invention.

Example 1

5-phenyl-6a-(1-phenylvinyl)-tetrahydrofuro[3,2-b]furan-2-one

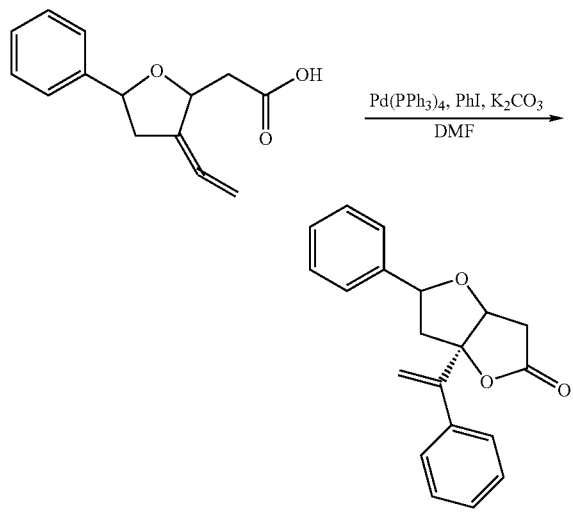

(5-phenyl-3-vinylidene-tetrahydro-furan-2-yl)acetic acid (32 mg, 0.12 mmol), Pd(PPh$_3$)$_4$ (14 mg, 0.012 mmol) and K$_2$CO$_3$ (84 mg, 0.61 mmol) were dissolved in 3 mL of dimethylformamide, followed by addition of PhI (68 μL, 0.61 mmol). The solution was stirred for 4 hours at 85° C. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:15, v/v), thus providing products (26 mg, 62%).

$^1$H NMR (300 MHz, CDCl$_3$): δ 7.47–7.28 (m, 10H), 5.57 (d, 1H, J=5.4 Hz), 5.37 (d, 1H, J=5.4 Hz), 4.97–4.90 (m, 1H), 4.80 (t, 1H, J=4.8 Hz), 2.96–2.68 (m, 3H), 2.58–2.49 (m, 1H).

Example 2

5-p-tolyl-6a-(1-phenylvinyl)-tetrahydrofuro[3,2-b]furan-2-one

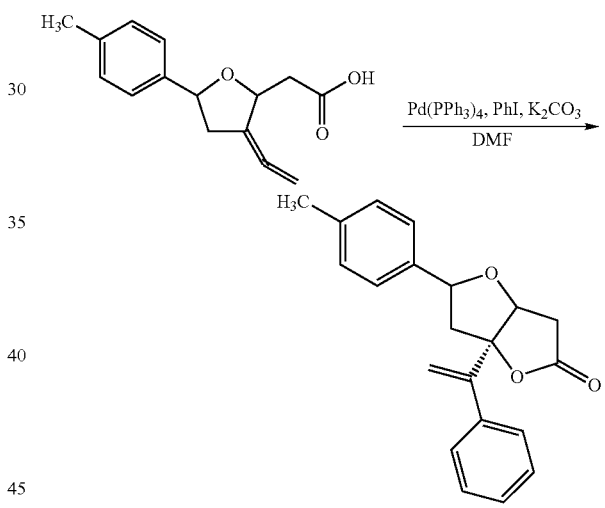

(5-p-tolyl-3-vinylidene-tetrahydro-furan-2-yl)acetic acid (35 mg, 0.14 mmol), Pd(PPh$_3$)$_4$ (14 mg, 0.012 mmol) and K$_2$CO$_3$ (84 mg, 0.61 mmol) were dissolved in 3 mL of dimethylformamide, followed by addition of PhI (68 μL, 0.61 mmol). The solution was stirred for 4 hours at 85° C. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:15, v/v), thus providing products (27 mg, 58%).

$^1$H NMR (300 MHz, CDCl$_3$): δ 7.71–7.62 (m, 2H), 7.38–7.17 (m, 8H), 5.70 (d, 1H), 5.30 (d, 1H), 4.94 (t, 1H), 4.38–4.34 (m, 1H), 2.70–2.52 (m, 3H), 2.37–2.25 (m, 3H).

Example 3

5-(4-methoxyphenyl)-6a-(1-phenylvinyl)-tetrahydro-furo[3,2-b]furan-2-one

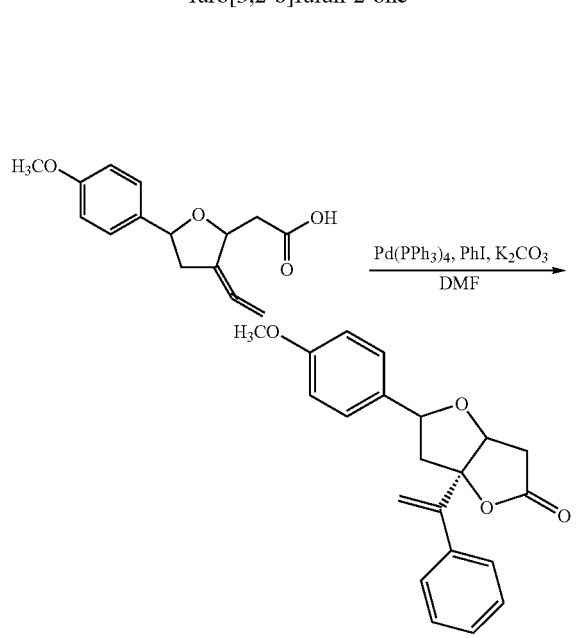

(5-(4-methoxyphenyl)-3-vinylidene-tetrahydro-furan-2-yl)acetic acid (34 mg, 0.12 mmol), Pd(PPh$_3$)$_4$ (14 mg, 0.012 mmol) and K$_2$CO$_3$ (84 mg, 0.61 mmol) were dissolved in 3 mL of dimethylformamide, followed by addition of PhI (68 µL, 0.61 mmol). The solution was stirred for 4 hours at 85° C. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:15, v/v), thus providing products (27 mg, 61%).

$^1$H NMR (300 MHz, CDCl$_3$): δ 7.71–7.64 (m, 2H), 7.36–6.82 (m, 7H), 5.70 (d, 1H), 5.30 (d, 1H), 4.89 (t, 1H), 4.37–4.35 (m, 1H), 3.79 (s, 3H), 2.72–2.51 (m, 3H), 2.35–2.22 (m, 1H).

Example 4

2-phenyl-3a-(1-phenyl-vinyl)-hexahydrofuro[3,2-b]pyran-5-one

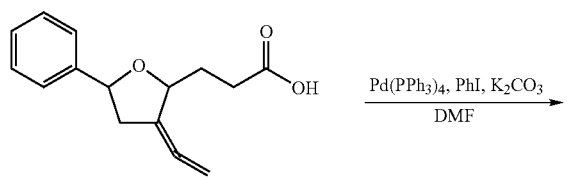

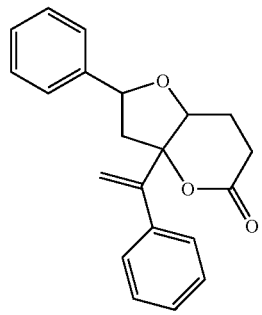

(5-phenyl-3-vinylidene-tetrahydro-furan-2-yl)propionic acid (60 mg, 0.25 mmol), Pd(PPh$_3$)$_4$ (29 mg, 0.025 mmol), K$_2$CO$_3$ (170 mg, 1.23 mmol) were dissolved in 6 mL of dimethylformamide, followed by addition of PhI (138 µL, 1.23 mmol). The solution was stirred for 4 hours at 85° C. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:15, v/v), thus providing products (52 mg, 67%).

$^1$H NMR (300 MHz, CDCl$_3$): δ 7.45–7.28 (m, 10H), 5.63 (s, 1H), 5.33 (s, 1H), 4.90 (t, 1H, J=7.5 Hz), 4.33 (t, 1H, J=3.3 Hz), 3.04 (m, 1H, J=6.0 Hz), 2.85–2.73 (m, 1H), 2.59–2.43 (m, 2H), 2.31–2.21 (m, 1H), 2.17–2.09 (m, 1H).

Example 5

2-p-tolyl-3a-(1-phenylvinyl)-hexahydrofuro[3,2-b]pyran-5-one

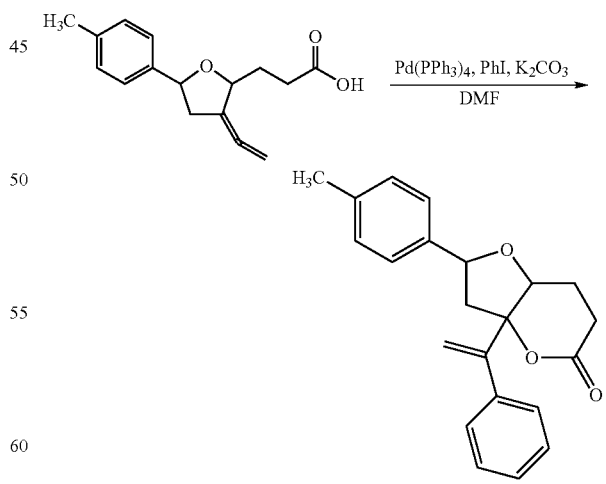

(5-p-tolyl-3-vinylidene-tetrahydro-furan-2-yl)propionic acid (61 mg, 0.25 mmol), Pd(PPh$_3$)$_4$ (29 mg, 0.025 mmol), K$_2$CO$_3$ (170 mg, 1.23 mmol) were dissolved in 6 mL of dimethylformamide, followed by addition of PhI (138 µL, 1.23 mmol). The solution was stirred for 4 hours at 85° C. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:15, v/v), thus providing products (50 mg, 63%).

$^1$H NMR (300 MHz, CDCl$_3$): δ 7.65 (d, 2H), 7.45–7.17 (m, 7H), 5.64 (s, 1H), 5.29 (s, 1H), 5.06 (t, 1H), 4.21–4.18 (m, 1H), 2.70–2.53 (m, 3H), 2.34 (s, 3H), 2.29–2.22 (m, 2H), 1.95–1.82 (m, 1H).

Example 6

2-(4-methoxyphenyl)-3a-(1-phenylvinyl)-hexahydro-furo[3,2-b]pyran-5-one

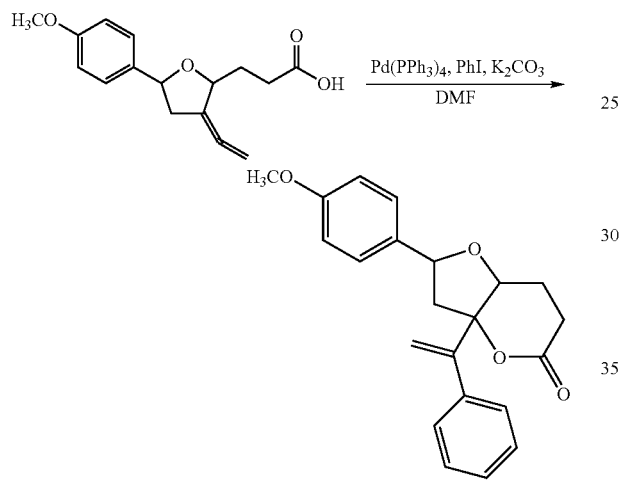

(5-(4-methoxyphenyl)-3-vinylidene-tetrahydro-furan-2-yl)propionic acid (61 mg, 0.25 mmol), Pd(PPh$_3$)$_4$ (29 mg, 0.025 mmol), K$_2$CO$_3$ (170 mg, 1.23 mmol) were dissolved in 6 mL of dimethylformamide, followed by addition of PhI (138 μL, 1.23 mmol). The solution was stirred for 4 hours at 85° C. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:15, v/v), thus providing products (57 mg, 73%).

$^1$H NMR (300 MHz, CDCl$_3$): δ 7.65 (d, 2H), 7.45–7.17 (m, 5H), 6.80 (d, 2H), 5.64 (s, 1H), 5.29 (s, 1H), 5.01 (t, 1H), 4.22–4.19 (m, 1H), 3.79 (s, 3H), 2.76–2.53 (m, 3H), 2.34 (s, 3H), 2.25–2.21 (m, 2H), 1.93–1.81 (m, 1H).

As set forth above, the present invention relates to stereoselective bicyclic tetrahydrofuran lactone derivatives with cis geometry at C-2,5, and a simple and efficient preparation method thereof by performing an intramolecular cyclization of tetrahydrofuran-allenic acid derivatives in the presence of a phenyl halide, a palladium catalyst and a base. Especially, the bicyclic tetrahydrofuran lactone derivatives may serve as an important intermediate compound in synthesis of natural substance.

What is claimed is:

1. Bicyclic tetrahydrofuran lactone of Formula (1):

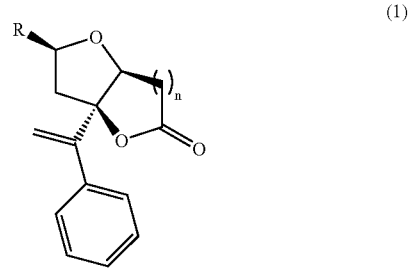

wherein n is 1 or 2, and R is phenyl optionally substituted with C$_1$–C$_6$ alkyl, C$_1$–C$_6$ alkoxy, hydroxyl or C$_1$–C$_6$ hydroxyalkyl group.

2. The bicyclic tetrahydrofuran lactone of claim 1, wherein n is 1, and R is phenyl optionally substituted with C$_1$–C$_6$ alkyl or C$_1$–C$_6$ alkoxy group.

3. The bicyclic tetrahydrofuran lactone of claim 1, wherein n is 2, and R is phenyl optionally substituted with C$_1$–C$_6$ alkyl or C$_1$–C$_6$ alkoxy group.

4. A process of preparing bicyclic tetrahydrofuran lactone of Formula (1), the process comprising an intramolecular cyclization of tetrahydrofuran-allenic acid derivatives of Formula (2) in the presence of a phenyl halide, a palladium catalyst and a base:

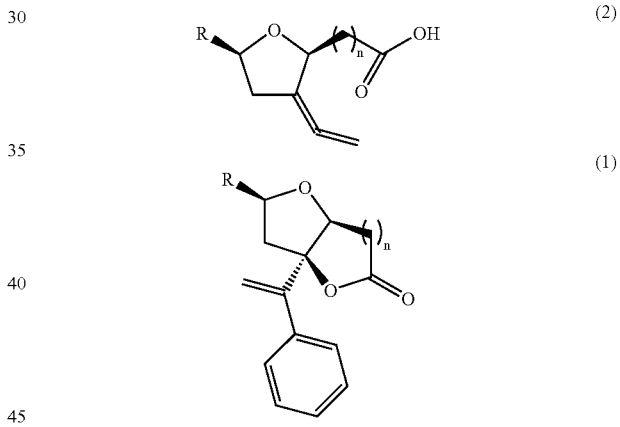

wherein n is 1 or 2; R is phenyl optionally substituted with C$_1$–C$_6$ alkyl, C$_1$–C$_6$ alkoxy, hydroxyl or C$_1$–C$_6$ hydroxyalkyl group; and R$_1$ is C$_1$–C$_6$ alkyl group.

5. The process of claim 4, wherein any solvent selected from diethyl ether, tetrahydrofuran, dichloromethane, dimethylformamide, ethyl acetate, chloroform and a mixture thereof may be used.

6. The process of claim 4, wherein the phenyl halide is used in an amount of about 1–6 equivalents.

7. The process of claim 4, wherein 0.01–1 equivalent of tetrakis(triphenylphosphin)palladium is used as the palladium catalyst.

8. The process of claim 4, wherein the base is metal salt selected from the group of carbonate, bicarbonate, sulfate and a mixture thereof and wherein the metal is alkali metal or alkaline earth metal.

9. The process of claim 8, wherein 1–6 equivalents of potassium carbonate is used as the base.

10. The process of claim 4, wherein the cyclization is performed at 0–90° C.

* * * * *